United States Patent [19]

Helfrich

[11] Patent Number: 5,308,338
[45] Date of Patent: May 3, 1994

[54] CATHETER OR THE LIKE WITH MEDICATION INJECTOR TO PREVENT INFECTION

[76] Inventor: G. Baird Helfrich, 4001 89th St., Lubbock, Tex. 79423

[21] Appl. No.: 50,659
[22] Filed: Apr. 22, 1993
[51] Int. Cl.$^5$ ................ A61M 5/32; A61M 25/00
[52] U.S. Cl. .................................... 604/175; 604/265
[58] Field of Search ............... 604/29, 93, 174, 175, 604/264, 265, 268, 269, 280; 128/DIG. 26

[56] References Cited

U.S. PATENT DOCUMENTS

| Re. 34,037 | 8/1982 | Inoue et al. |
|---|---|---|
| 3,394,705 | 6/1968 | Abramson . |
| 3,447,161 | 6/1969 | Weikel . |
| 3,699,956 | 10/1972 | Kitrilakis et al. . |
| 3,981,299 | 9/1976 | Murray . |
| 4,266,999 | 5/1981 | Baier ........................ 156/227 |
| 4,423,725 | 1/1984 | Baran et al. . |
| 4,501,580 | 2/1985 | Glassman . |
| 4,584,998 | 4/1986 | McGrail . |
| 4,592,920 | 6/1986 | Murtfeldt . |
| 4,623,329 | 11/1986 | Drobish et al. .............. 604/29 |
| 4,676,782 | 6/1987 | Yamamoto et al. .......... 604/175 |
| 4,687,471 | 8/1987 | Twardowski et al. . |
| 4,725,264 | 2/1988 | Glassman . |
| 4,753,640 | 6/1988 | Nichols et al. . |
| 4,755,171 | 7/1988 | Tennant ...................... 604/93 |
| 4,772,269 | 9/1988 | Twardowski et al. . |
| 4,795,439 | 1/1989 | Guest . |
| 4,798,585 | 1/1989 | Inoue et al. . |
| 4,906,238 | 3/1990 | Greenfeld et al. . |
| 5,004,455 | 4/1991 | Greenwood et al. . |
| 5,049,140 | 9/1991 | Brenner et al. . |
| 5,057,075 | 10/1991 | Moncrief et al. ............ 604/49 |
| 5,085,632 | 2/1992 | Ikada et al. . |
| 5,085,646 | 2/1992 | Svenson et al. ............. 604/175 |
| 5,098,379 | 3/1992 | Conway et al. ............. 604/51 |
| 5,098,413 | 3/1992 | Trudell et al. . |
| 5,108,369 | 4/1992 | Ganguly et al. . |
| 5,141,499 | 8/1992 | Zappacosta . |
| 5,143,062 | 9/1992 | Peckham . |
| 5,146,916 | 9/1992 | Catalani . |
| 5,156,597 | 10/1992 | Verreet et al. .............. 604/175 |
| 5,176,638 | 1/1993 | Michael ...................... 604/101 |
| 5,178,611 | 1/1993 | Rosenberg .................. 604/172 |
| 5,236,422 | 8/1993 | Eplett, Jr. ................... 604/265 |

Primary Examiner—John D. Yasko
Assistant Examiner—Adam J. Cermak
Attorney, Agent, or Firm—Mason, Fenwick & Lawrence

[57] ABSTRACT

A peritoneal dialysis catheter has annular cuffs at one or more locations along its length. The cuffs are of a woven material to promote tissue ingrowth and thereby anchor the catheter to the body. The catheter has internal channels extending from ports located outside the body to deliver disinfecting fluid to the space between the cuffs and the catheter exterior, preventing infections from reaching the cuffs and reducing the frequency of new implants.

24 Claims, 2 Drawing Sheets

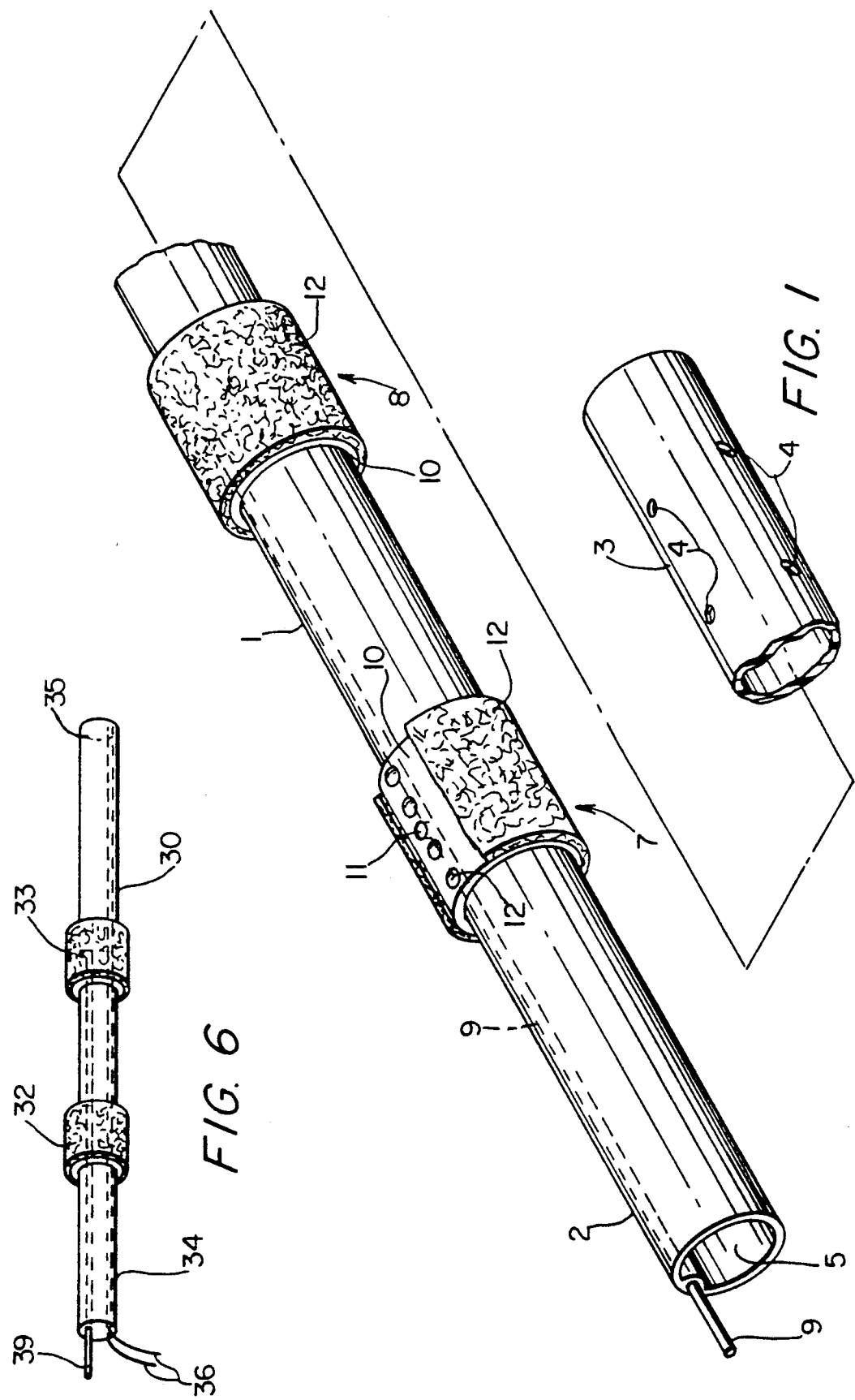

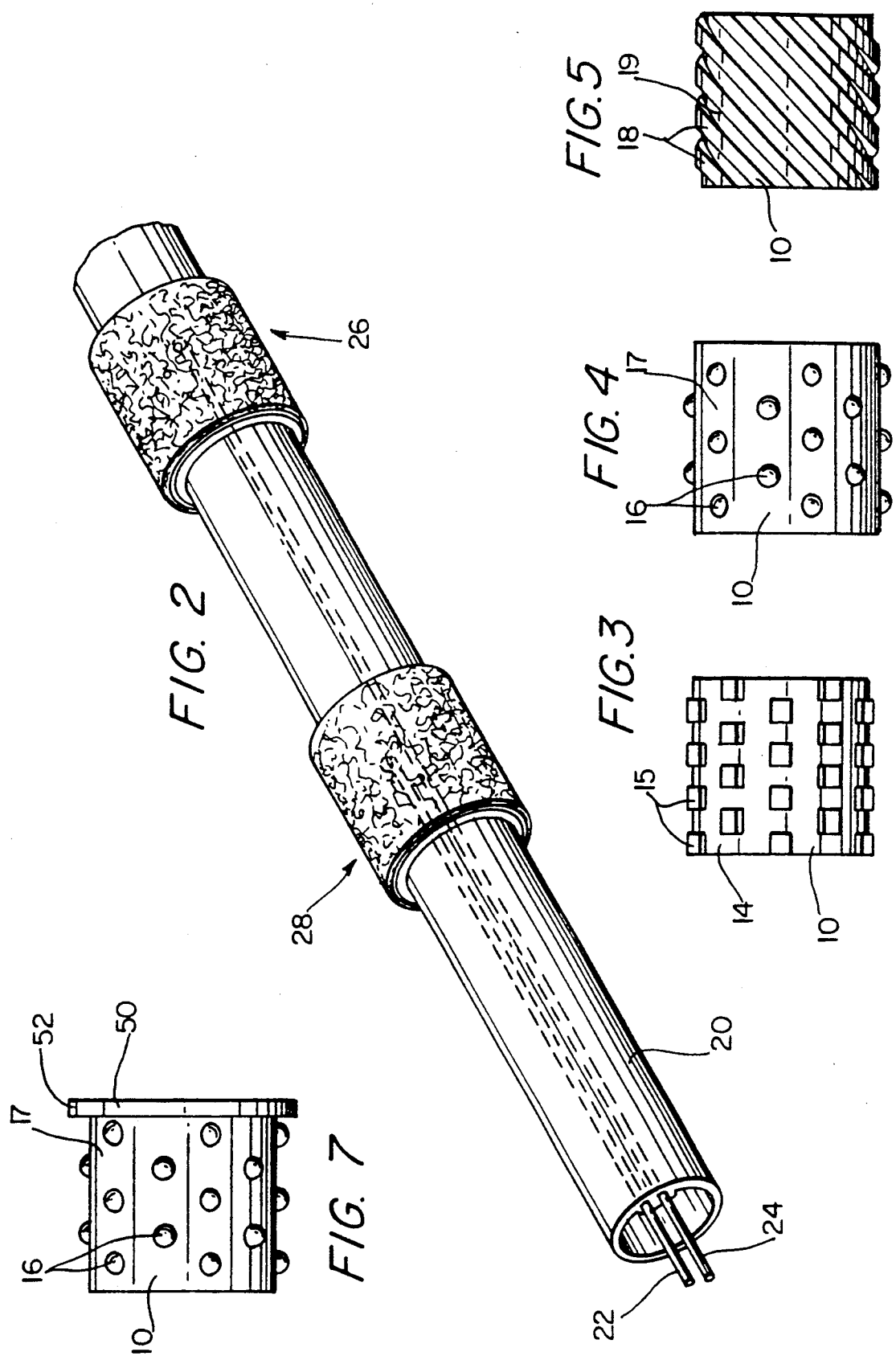

CATHETER OR THE LIKE WITH MEDICATION INJECTOR TO PREVENT INFECTION

BACKGROUND OF THE INVENTION

1. Field of the Invention

The present invention relates to surgically implanted catheter and like tubular devices, specifically to catheters or similar live body implantable devices including means for preventing infectious bacteria and other microorganisms from entering and penetrating into the body through the exit wound site of the implanted device. It is even more specifically in its preferred embodiment directed to a catheter for peritoneal dialysis.

Peritoneal dialysis has offered promise for improving the mobility of patients suffering from kidney disease or failure. Like hemodialysis, peritoneal dialysis involves the diffusional removal of waste products in the patient's blood. Instead of removing and treating the blood outside the body, however, dialysate is introduced directly into the peritoneal cavity by a catheter.

The dialysate fluid remains in the peritoneal cavity for a desired period of time as waste products diffuse from the blood across the peritoneum and into the dialysate. When the dialysate reaches chemical equilibrium, it is removed from the body, fresh dialysate is introduced, and the cycle is repeated.

Peritoneal catheters generally involve a tubular body with one or more dialysate ports outside the patient's body which communicate through the tubular body with the peritoneal cavity. A tunnel cavity is surgically created within the abdominal cutaneous and subcutaneous tissues, including the peritoneum. The catheter is then inserted within the cavity and either stitched to body tissues or anchored in place by the use of porous "cuffs" into which tissue growth is facilitated.

Because peritoneal catheters create a tunnel exit site from the body, there exists a potential for the invasion of infectious bacteria and other microorganisms. Furthermore, the movement of the patient's body from ordinary breathing, walking, and other like activities result in small back-and-forth movements, called "pistoning," of the catheter with respect to the cutaneous and subcutaneous body tissues, which aggravates the risk of bacterial invasion.

Many prior attempts to reduce rates of infections for peritoneal dialysis catheters involve the use of "cuffs"—porous segments fitted annularly around the body of the catheter. After implantation, tissue ingrowth into the porous material anchors the catheter to the body, preventing excessive movement. Additionally, the cuffs act as a putative seal against penetration of infectious microorganisms further into the body.

Catheter designs for peritoneal dialysis are known in the art, as are attempts to reduce the risk of bacterial invasion associated with their use. Illustrative are the designs disclosed in U.S. Pat. No. 5,141,499 to Zappacosta; U.S. Pat. No. 5,098,413 to Trudell, et al.; U.S. Pat. No. 5,057,075 to Moncrief et al.; U.S. Pat. No. 5,049,140 to Brenner et al.; U.S. Pat. No. 4,772,269 and U.S. Pat. No. 4,687,471, both to Twardowski; and U.S. Pat. No. 4,623,329 to Drobish et al.

U.S. Pat. No. 5,141,499 to Zappacosta discloses a U-shaped catheter (10) for peritoneal dialysis With two cuffs (18, 30) and a reduced-diameter tube (16) at the exit site from the body to reduce the area for exit-site tunnel infections.

U.S. Pat. No. 5,098,413 to Trudell et al. discloses a catheter (10) for peritoneal dialysis with a bent shape (29) to reduce catheter movement within the body during dialysate introduction and removal. Two cuffs (30) are used to prevent bacteria ingrowth and to hold the catheter (10) in the body.

U.S. Pat. No. 5,057,075 to Moncrief et al. relates to a method of implanting a peritoneal dialysis catheter with two cuffs, one cuff (2) being adjacent the skin and a peritoneal cuff (24) being anterior to the posterior rectus sheath (23).

U.S. Pat. No. 5,049,140 to Brenner et al. discloses elastomeric fittings (12) of cylindrical shape which are impregnated with antimicrobial agents and fit by radial tension as cuffs over the body shaft (14) of a catheter (10).

U.S. Pat. No. 4,772,269 to Twardowski et al. discloses a peritoneal catheter (10) with a bent segment (24) and two porous cuffs (20, 22) to secure the catheter to the abdominal wall.

U.S. Pat. No. 4,687,471 to Twardowski et al. discloses a peritoneal dialysis catheter (15) with a bent segment (24) and two porous cuffs (20, 22) to secure the catheter to the abdominal wall. The device is substantially similar to U.S. Pat. No. 4,772,269 above, of the same inventor, but includes a flange (38, 48) and a bead (44), the flange oriented at an angle to the axis of the catheter tube (12).

U.S. Pat. No. 4,623,329 to Drobish et al. discloses a tube-in-tube catheter, the outer sleeve (10) of which is permeable by diffusion to an antimicrobial agent contained in the annulus (13) between the inner drainage tube (2) and the outer sleeve (10).

Unfortunately, the practice of using cuffs to reduce the risks of bacterial infection in the catheter suffers from several drawbacks. Although cuffs do provide a measure of resistance to bacterial invasion, they do not prevent bacteria from entering the wound at the exit site, nor do they destroy bacteria traveling along the shaft of the catheter toward the cuffs from the exit site. The use of multiple cuffs to provide "staged" protection against invasion has been suggested. It has also been suggested that the cuffs have antimicrobial agents embedded within their pores as discussed in U.S. Pat. No. 5,049,140 to Brenner et al. The effectiveness of such agents, of course, falls off rapidly as their concentration is reduced over time.

Multiple cuffs provide additional rigidity to the catheter, arising from the greater proportion of the total length of the catheter that is subject to tissue ingrowth into the cuffs. They do little to obviate the disadvantages noted above, however. Because of these failures, multiple cuffs can at best only delay the inevitable need for removal of the catheter arising from infection. When this becomes necessary, the greater tissue ingrowth associated with multiple cuffs impedes and complicates the removal and process. In addition, each removal and replacement operation involves additional trauma for patients already suffering from the loss of renal function.

It is therefore an object of this invention to overcome the disadvantages attendant upon the use of cuffs and to prevent indefinitely the onset of infections in peritoneal dialysis and like catheters, while retaining the advantageous properties and functions thereof. It is a further object of the invention to provide an improved catheter for use in peritoneal dialysis which will withstand a much longer indwelling time within the body before removal is required, thus reducing the trauma to the patient.

SUMMARY OF THE INVENTION

The present invention is directed to a catheter having proximal and distal ends and employing annular cuffs adapted for tissue ingrowth to better secure the device within the patient's body and prevent infection. The catheter has a tubular body, with one or more primary channels extending the length of the tube and having at the proximal end ports for introducing or removing dialysate or other fluids, and at the distal end one or more openings which communicate with the peritoneal cavity when the device is implanted.

Secondary channels, having ports at the proximal end for introducing antiseptic fluid, communicate with the exterior surface of the tube. The channels deliver the fluid to a dispersing cuff means disposed between the body of the tube and the cuffs. The dispersing cuff means comprises a base sleeve having a port communicating with a secondary channel on which a porous cylindrical pad is mounted; in some embodiments the base sleeve includes protrusions on the upper ends of which the porous cylindrical pad is mounted with flow passageways for the fluid being provided between the protrusions so that the antiseptic disinfecting fluid from the port can flow easily into the porous pad and adjacent areas between the tube and the cuffs, and directs the fluid back along the tube toward the tunnel exit site.

A second embodiment is in the form of a solid flexible wire or the like having sensor means or the like on or in its distal end and which includes at least one secondary channel communicating with first and second dispensing cuff means as described above; however, the second embodiment does not have a primary channel in its interior or elsewhere.

BRIEF DESCRIPTION OF THE DRAWINGS

The foregoing summary, as well as the following detailed description of a preferred embodiment of the invention, will be better understood when read in conjunction with the appended drawings, in which:

FIG. 1 is a perspective view of a peritoneal catheter utilizing two cuffs and having channels for delivering disinfecting fluid to the inner surface of the cuffs;

FIG. 2 is a perspective view of a second embodiment of the catheter;

FIG. 3 is a top plan view of an alternate form for the outer cuff component;

FIG. 4 is a top plan view of a third cuff outer component embodiment fluid dispersing means comprising raised spherical projection which provide flow channels for the disinfecting fluid;

FIG. 5 is a top plan view of a fourth cuff outer component embodiment fluid dispersing means comprising a group of diagonal, raised ribs on the exterior surface of the catheter, which provide linear disinfectant flow channels between the raised ribs; and FIG. 6 is a perspective view of a solid sensor second embodiment of the invention; and FIG. 7 is a top plan view of a variation of the cuff components of FIGS. 1, 3, 4 and 5.

DETAILED DESCRIPTION OF THE PREFERRED EMBODIMENTS

The preferred embodiment of the invention comprises of catheter 1 which is specifically designed for use in peritoneal dialysis. As shown in FIG. 1, catheter 1 has a proximal end 2 and an open distal end 3 in which a plurality of radial openings 4 are provided to extend through the tubular catheter wall. Catheter 1 is fabricated of a material compatible with the human body such as silicone rubber or like polymers. Many different shapes and materials known in the art may be used. The catheter is of a tubular shape, and has a primary interior channel 5 which, after implantation, communicates with the peritoneal cavity at the openings in distal end 3. Proximal end 2 is adapted to be disposed outside the human body, and is provided with one or more ports (not shown) in communication with channel 5 for the introduction and/or removal of dialysate or other fluids to or from the peritoneal cavity.

The catheter 1 is held in position within the abdominal wall of the body by means of an outer cuff 7 and an inner cuff 8 disposed annularly and exteriorly around a segment of the exterior surface 3 of the catheter 1 and each engaging the abdominal wall so that the outer cuff 7 is positioned adjacent the outer extent of the abdominal wall and the inner cuff 8 is positioned adjacent the inner extent of the abdominal wall. The cuffs 7 and 8 are identical and each include a base sleeve 10 fixedly secured by adhesive or the like to the outer surface of catheter 1 and formed of the same or compatible nonporous material as the catheter. A plurality of ports 11 are provided in each base sleeve 10 and extend through the catheter wall to communicate with a secondary channel or tube 9 which is provided in the catheter body.

Each base sleeve member 10 of each of cuffs 7 and 8 is surrounded by a porous cylindrical pad 12 formed of randomly oriented bonded fibers held together by a compatible bonding agent. Any of the well known materials having the capacity of permitting the ingrowth of tissue could be used for the porous cylindrical pads. The porous cylindrical pad portion of the cuffs can, for example, be formed of polymer wool, or PTFE, scintered metal or even ceramic material or other materials.

Variations in the base sleeves are illustrated in FIGS. 3, 4 and 5. More specifically, FIG. 3 illustrates a second embodiment of the base sleeve in which a plurality of square protrusions 15 extend outwardly with the spaces 14 between protrusions 15 defining flow passageways for liquid flowing from ports 11 for disinfecting the porous pad 12 is attached to and supported on the upper ends of protrusions 15 in a matter to be discussed in detail hereinafter. Similarly, FIG. 4 illustrates a third embodiment of the base sleeves in which semicircular protrusions 16 extend outwardly from a base sleeve 10 with spaces 17 between the semicircular protrusions defining flow passageways for disinfecting liquid. Lastly, FIG. 5 illustrates a fourth embodiment of the base sleeve in which linear strip members 18 extend outwardly and are separated by the flow passageways 19 through which the disinfectant can flow.

All of the base sleeve embodiments of FIGS. 3, 4 and 5 are useable with the catheter embodiments of FIG. 1 and FIG. 2. It should be noted that the catheter embodiment of FIG. 1 employs only a single secondary channel 9 which is connected in series to the ports 11 of both the outer cuff 7 and inner cuff 8. Thus, disinfectant introduced through secondary channel 9 is discharged outwardly into cuffs 7 and 8 for disinfecting the body opening through which the catheter 1 extends.

FIG. 7 illustrates a variation of the cuff embodiments of FIGS. 3, 4, 5 and 6 in which an annular fluid impervious seal 50 extends radially outward from the distal end of sleeve member 10. The cylindrical outer surface 52 of seal 50 positioned to engage the surrounding tissue of the body wall in which it is positioned to preclude the passage of disinfectant fluid inwardly into the body of the patient. The radius of the outer surface 52 should preferably be at least equal to the radius of the porous cylindrical pad 12 in its uncompressed condition.

FIG. 2 illustrates a catheter 20 which is identical to catheter 1 with the exception of the fact that it incorporates first and second secondary channels 22 and 24 which are respectively connected in parallel to the ports 11 in inner and outer cuffs 26 and 28. Thus, each of the secondary channels 22 and 24 serves to provide disinfectant fluid to one of the cuff members. Cuff members 26 and 28 are respectively identical to cuff members 7 and 8 of the first embodiment.

In all of the embodiments, the disinfectant is introduced through the secondary channels to flow outwardly and to the porous cylindrical pad of the respective cuff members to eradicate bacteria or other infectious organisms that might be present in the porous cylindrical pads and the tissue and structure adjacent thereto.

FIG. 6 illustrates a second embodiment body implant comprising a solid sensor 30 having an outer cuff 32 and an inner cuff 33 identical to the previously described cuffs attached to its outer surface. Also, sensor 30 has a distal end 35 and a proximal end 34 with wires 36 extending from the proximal end for connection to conventional monitoring means. Also, the distal end 35 would incorporate any one or more sensor means for monitoring various body functions in a well known manner. When the embodiment of FIG. 6 is embedded in a living body, the cuffs 32 and 33 are positioned in the wall of the living body in precisely the same manner as the previously discussed embodiments. A secondary channel 39 is provided to extend through the body of the sensor for providing fluid to the cuffs. Moreover, a pair of secondary channels could be provided in the manner of the embodiment of FIG. 2.

It should be understood that the foregoing porous cylindrical pad constructions are merely exemplary and other constructions could obviously be used without departing from the spirit and scope of the invention. Similarly, other obvious variations from the disclosed catheter and solid sensor embodiments will occur to those of skill in the art. Therefore, it should be understood that the spirit and scope of the invention is to be limited solely by the following claims.

What is claimed is:

1. A catheter comprising:
   a) a tubular body having a tube wall, proximal and distal ends, and an exterior surface, adapted to be positioned in an operative position in a living body wall such that said proximal end is positioned outside the living body and said distal end lies within the living body inwardly of the body wall;
   b) at least one primary interior channel within said tubular body, extending substantially the entire length of said tubular body and having openings at said proximal and distal ends, the opening at said distal end being positioned to communicate with the interior of the living body when said tubular body is in its operative position;
   c) a cuff having proximal and distal ends and comprising an inner base sleeve and a outer porous cylindrical pad mounted on said inner base sleeve and flow ports extending through said inner base sleeve and said tubular body; said inner base sleeve being disposed annularly and engagingly around said tubular body, and adapted to be located within the body wall of the living body when said tubular body is in its operative position;
   d) a secondary channel within said tubular body, extending from said proximal end a distance along said tubular body and being positioned to communicate with said flow ports extending through said tube wall at a point located between said proximal and distal ends of said cuff, said secondary channel permitting the introduction of disinfectant fluid through said flow ports to engage and cleanse the body wall.

2. The catheter of claim 1, additionally including a second cuff having proximal and distal ends and comprising a second inner base sleeve and a second outer porous cylindrical pad mounted on said second inner base sleeve and second flow port means extending through said second inner base sleeve and said tubular body and communicating with said secondary channel; said second inner base sleeve being bonded to said tubular body at a location spaced axially from said first base sleeve so that said cuffs are positioned to engage inner and outer portions of the interior of the body wall of the living body when said catheter is in its operative position.

3. A catheter as recited in claim 2, wherein said porous pad is formed of randomly oriented fibrous material compatible with the ingrowth of human tissue when said tubular body is in its operative position.

4. A catheter as recited in claim 2, wherein at least one of said base sleeves includes a plurality of square in cross-section protrusions separated by open flow-permitting spaces with said porous pad being mounted on the outer ends of said protrusions.

5. A catheter as recited in claim 2, wherein at least one of said base sleeves includes a plurality of semicircular protrusions separated by open flow-permitting spaces, with said porous pad being mounted on the outer ends of said protrusions.

6. A catheter as recited in claim 2, wherein at least one of said base sleeves includes a plurality of raised strips between which spiral open flow passages are provided with said porous pad being mounted on the upper extent of said raised strips.

7. A catheter as recited in claim 2 wherein said cuffs are spaced apart so as to be engageable with inner and outer interior portions of the abdominal wall of a human being, whereby said catheter is usable for peritoneal dialysis.

8. A catheter as recited in claim 7, wherein said porous pad is formed of randomly oriented fibrous material compatible with the ingrowth of living tissue when said tubular body is in its operative position.

9. The catheter of claim 7 additionally including a second cuff having proximal and distal ends and comprising a second inner base sleeve and a second outer porous cylindrical pad mounted on said second inner base sleeve and second flow port means extending through said second inner base sleeve and adjacent portions of said tubular body; a second secondary channel extending length-wise of said tubular body and isolated from said primary interior channel and communicating with said second flow port means, said second base sleeve being bonded to said tubular body at a location spaced axially from said first base sleeve so that said first and second cuffs are positioned to engage inner and outer portions of the interior of the body wall of the living body when said catheter is in its operative position.

10. A catheter as recited in claim 9, wherein said porous pad is formed of randomly oriented fibrous material compatible with the ingrowth of human tissue when said tubular body is in its operative position.

11. The catheter of claim 1 additionally including a second cuff having proximal and distal ends and comprising a second inner base sleeve and a second outer porous cylindrical pad mounted on said second inner base sleeve and second flow port means extending through said second inner base sleeve and adjacent portions of said tubular body; a second secondary channel extending length-wise of said tubular body and isolated from said primary interior channel and communicating with said second flow port means, said second base sleeve being bonded to said tubular body at a location spaced axially from said first base sleeve so that said first and second cuffs are positioned to engage inner and outer portions of the interior of the body wall of the living body when said catheter is in its operative position.

12. A catheter as recited in claim 11, wherein said porous pad is formed of randomly oriented fibrous material compatible with the ingrowth of living tissue when said tubular body is in its operative position.

13. A catheter as recited in claim 11, wherein at least one of said base sleeves includes a plurality of square cross-section protrusions separated by open flow-permitting spaces with said porous pad being mounted on the outer ends of said protrusions.

14. A catheter as recited in claim 11, wherein at least one of said base sleeves includes a plurality of semicircular protrusions separated by open flow-permitting spaces with said porous pad being mounted on the outer ends of said protrusions.

15. A catheter as recited in claim 11, wherein at least one of said base sleeves includes a plurality of raised strips between which spiral open flow passages are provided with said porous pad being mounted on the upper extent of said raised strips.

16. A catheter as recited in claim 1 additionally including a radial annular fluid impervious seal having an outer surface engageable with the living body wall provided adjacent the proximal end of said cuff and dimensioned so that it prevents passage of disinfectant fluid inwardly from the body wall beyond the cuff.

17. The catheter of claim 16, additionally including a second cuff having proximal and distal ends and comprising a second inner base sleeve and a second outer porous cylindrical pad mounted on said second inner base sleeve and second flow port means extending through said second inner base sleeve and said tubular body and communicating with said secondary channel; said second inner base sleeve being bonded to said tubular body at a location spaced axially from said first base sleeve so that said cuffs are positioned to engage inner and outer portions of the interior of the body wall of the living body when said catheter is in its operative position.

18. The catheter of claim 16 additionally including a second cuff having proximal and distal ends and comprising a second inner base sleeve and a second outer porous cylindrical pad mounted on said second inner base sleeve and second flow port means extending through said second inner base sleeve and adjacent portions of said tubular body; a second secondary channel extending length-wise of said tubular body and isolated from said primary interior channel and communicating with said second flow port means, said second base sleeve being bonded to said tubular body at a location spaced axially from said first base sleeve so that said first and second cuffs are positioned to engage inner and outer portions of the interior of the body wall of the living body when said catheter is in its operative position.

19. A catheter as recited in claim 18, wherein said porous pad is formed of randomly oriented fibrous material compatible with the ingrowth of living tissue when said tubular body is in its operative position.

20. An elongated, cylindrical body implant having an outer surface, a primary channel within said body implant extending substantially the entire length of said body implant, a distal end and a proximal end, which implant is adapted to be positioned in an operative position in a living body wall such that said proximal end is positioned outside the living body and said distal end lies within the living body inwardly of the body wall; said implant including:
   a) a cuff having proximal and distal ends and comprising an inner base sleeve and an outer, porous, cylindrical pad mounted externally on said inner base sleeve, wherein said inner base sleeve is secured to the outer surface of the body implant, flow ports extending through said inner base sleeve to said body implant; said inner base sleeve being disposed annularly and engagingly around said body implant, and adapted to be located within the body wall of the living body when said body implant is in its operative position; and
   b) a secondary channel within said body implant, extending from said proximal end a distance along said body implant and being positioned to communicate with said flow ports at a point located between said proximal and distal ends of said cuff.

21. An elongated, cylindrical body implant as recited in claim 20, additionally including a second cuff having proximal and distal ends and mounted on said outer surface of said body implant and comprising a second inner base sleeve and a second outer porous cylindrical pad mounted on said second inner base sleeve and second flow port means extending through said second inner base sleeve to said body implant and communicating with said secondary channel; said second inner base sleeve being bonded to said body implant at a location spaced axially from said first base sleeve so that said first and second cuffs are positioned to engage inner and outer portions of the interior of the body wall of the living body when said body implant is in its operative position.

22. A body implant as recited in claim 21, wherein said porous pad is formed of randomly oriented fibrous material compatible with the ingrowth of human tissue when said body implant is in its operative position.

23. A body implant as recited in claim 21, wherein at least one of said base sleeves includes a plurality of square in cross-section protrusions separated by open flow-permitting spaces with said porous pad being mounted on the outer ends of said protrusions.

24. A body implant as recited in claim 21, wherein at least one said base sleeve includes a plurality of raised strips between which linear open flow pass are provided with said porous pad being mounted on the upper extent of said raised strips.

* * * * *